United States Patent [19]

Yang

[11] 4,400,503
[45] Aug. 23, 1983

[54] PURIFICATION OF SYN-7-[[(2-AMINO-4-THIAZOLYL)(METHOXYIMINO) ACETYL]AMINO]-3-METHYL-3-CEPHEM-4-CARBOXYLIC ACID

[75] Inventor: Kuo S. Yang, Greenwood, Ind.

[73] Assignee: Eli Lilly and Company, Indianapolis, Ind.

[21] Appl. No.: 316,615

[22] Filed: Oct. 30, 1981

[51] Int. Cl.³ .......................................... C07D 501/12
[52] U.S. Cl. ................................................... 544/28
[58] Field of Search ....................................... 544/28

[56] References Cited

U.S. PATENT DOCUMENTS

| | | | |
|---|---|---|---|
| 4,202,893 | 5/1980 | Heymes et al. | 424/246 |
| 4,205,180 | 5/1980 | Ochiai et al. | 560/168 |
| 4,278,671 | 7/1981 | Ochiai et al. | 424/246 |
| 4,298,606 | 11/1981 | Ochiai et al. | 424/246 |
| 4,298,607 | 11/1981 | Natsugari | 544/27 |

FOREIGN PATENT DOCUMENTS 2036746 7/1980 United Kingdom.
2064513 6/1981 United Kingdom.

*Primary Examiner*—Paul M. Coughlan, Jr.
*Attorney, Agent, or Firm*—Nancy J. Harrison; Arthur R. Whale

[57] ABSTRACT

Crystalline cephalosporin hydrochloride salt represented by the formula

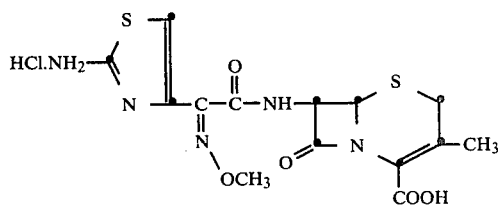

wherein the oxime is in the syn configuration, is a useful pharmaceutical form of, and tool for purification of, the corresponding antibiotic free base; processes for its preparation are provided.

4 Claims, No Drawings

PURIFICATION OF SYN-7-[[(2-AMINO-4-THIAZOLYL)(METHOXYIMINO)ACETYL]AMINO]-3-METHYL-3-CEPHEM-4-CARBOXYLIC ACID

SUMMARY OF THE INVENTION

This invention provides a crystalline cephalosporin antibiotic, the hydrochloride salt represented by formula 1:

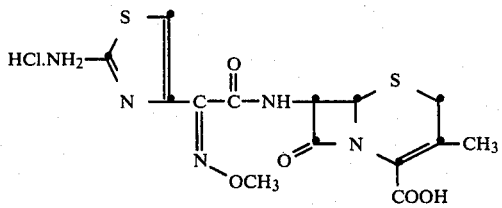

wherein the oxime is in the syn configuration. This invention also relates to a process for preparing the crystalline hydrochloride salt of formula 1 substantially free from other impurities.

DETAILED DESCRIPTION

This invention relates to a crystalline antibiotic salt. In particular, it relates to a crystalline cephalosporin antibiotic, the hydrochloride salt represented by formula 1. This compound is prepared from the cephalosporin antibiotic of formula 2:

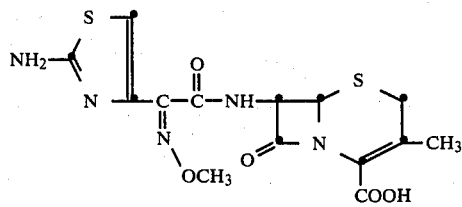

wherein the oxime is in the syn configuration, according to the process of this invention. The cephalosporin antibiotic of formula 2 is described by Heymes et al. in U.S. Pat. No. 4,202,893, issued May 13, 1980, and by Ochiai et al. in U.S. Pat. No. 4,205,180, issued May 27, 1980 and in U.S. Pat. No. 4,278,671, issued July 14, 1981.

As with most β-lactam antibiotics, such as the penicillins and the cephalosporins, a salt form of the antibiotic is often the pharmaceutical form which is administered. Crystalline salts are especially advantageous because such salts are more stable in addition to being compatible with and soluble in physiological fluids. Certain crystalline cephalosporin salts, including crystalline hydrochlorides, have been described [see, for example, West German Pat. No. 2,949,485 (Derwent Abstract 45382C/26), Belgian Pat. No. 885,488 (Derwent Abstract 27245D/16) and U.K. Pat. No. 1,589,841, published May 20, 1981]. The ability to form useful crystalline salts, however, is not predictable.

Purification of compounds to obtain products of pharmaceutically-acceptable quality is essential. With cephalosporin antibiotics such as the compounds of formulas 1 and 2, purification procedures are both time-consuming and expensive.

Crystalline substances aid greatly in purifying materials to obtain compounds in substantially pure form. My discovery of the compound of formula 1 in crystalline form, therefore, provides methods of obtaining both the hydrochloride of formula 1 and the free base of formula 2 in substantially pure form.

The hydrochloride salt of this invention is formally named syn-7-[[(2-amino-4-thiazolyl)(methoxyimino)acetyl]amino]-3-methyl-3-cephem-4-carboxylic acid hydrochloride. For convenience herein this compound is referred to as the hydrochloride salt.

The crystalline hydrochloride salt of this invention, when crystallized from formamide-water, has the following X-ray powder diffraction pattern ($Cu^{++}$ radiation, 1.5418Å, nickel filter d=interplanar spacing in angstroms):

| d | Relative Intensity |
|---|---|
| 13.56 | 25 |
| 8.61 | 25 |
| 7.78 | 75 |
| 6.88 | 45 |
| 5.80 | 15 |
| 5.13 | 7 |
| 4.42 | 100 |
| 4.29 | 35 |
| 4.10 | 55 |
| 3.98 | 35 |
| 3.87 | 40 |
| 3.64 | 35 |
| 3.47 | 60 |
| 3.16 | 62 |
| 3.07 | 18 |
| 3.00 | 15 |
| 2.91 | 15 |
| 2.80 | 18 |
| 2.74 | 22 |
| 2.60 | 12 |
| 2.50 | 20 |
| 2.45 | 20 |
| 2.39 | 15 |
| 2.23 | 15 |
| 2.15 | 15 |
| 2.12 | 15 |
| 2.00 | 20 |

The crystalline hydrochloride salt provided by this invention is a suitable pharmaceutical form which is stable at ordinary conditions of temperature and humidity. The salt can be stored in bulk form for later use, for example, in preparing unit-dosage forms in ampoules.

According to the process of this invention for preparing the crystalline hydrochloride salt, the cephalosporin compound of formula 2 is dissolved or slurried in water or a polar organic solvent, warming if necessary. The pH of this solution is adjusted to between about pH 1.5 and about 3.5 by the addition of hydrochloric acid. When the hydrochloride salt crystallizes, it is separated by standard methods.

The concentration of compound 2 in the solvent prior to the addition of the hydrochloric acid is preferably between about 15% and about 20% by weight; however, concentrations between about 10% and about 25% can also be used. When an organic solvent such as formamide is used, it is preferable to dilute the solution of the free base with water, preferably so that compound 2 is present in amounts of about 15% by weight, although more or less water can be used.

The term "polar organic solvent" includes solvents such as organic amides, lower alkanols, dimethyl sulfoxide, tetrahydrofuran, acetonitrile, acetone, dioxane, and the like, or a mixture of such solvents.

Organic amide solvents, such as formamide, acetamide, and dimethylformamide, are especially useful solvents in the process of this invention. For example, compound 2 is dissolved in formamide with warming; about two volumes of water are added to the formamide solution; hydrochloric acid is added until the solution has a pH of about 2; and compound 1 is allowed to crystallize.

Lower alkanols, such as ethanol, are also especially useful solvents in the process of this invention. Ethanol is particularly advantageous because it is relatively non-toxic. When ethanol is used, typically compound 2 is slurried in warm ethanol; concentrated hydrochloric acid is added to the slurry, dissolving compound 2 in the solution which forms; and compound 1 is allowed to crystallize.

Concentrated hydrochloride acid is preferably used in the process of this invention since more dilute solutions of the acid result in larger volumes of crystallization solution. It is especially desirable to avoid larger volumes, whenever possible, in large scale crystallizations. Hydrochloric acid solutions having a concentration of about 12 N are especially useful.

The process of this invention is carried out conveniently by warming the solution containing compound 1 to temperatures of about 30° to about 45° C. initially and subsequently cooling it to room temperature or below.

After crystallization, the hydrochloride salt crystals can be separated by filtration, centrifugation, or other suitable separation methods. After separation, the salt should be washed to remove any remaining mother liquor. Yields of crystalline hydrochloride salt realized from this process are generally in the range of from about 80 to about 90%.

The crystalline hydrochloride salt thus obtained generally contains water in amounts from about 2% to about 15%, with the average amount of water being about 5%. Except for the presence of water, the crystalline hydrochloride salt of this invention is obtained in substantially pure form, i.e. substantially free from impurities. The term "substantially pure" as used herein means that, after correcting for the presence of water, at least 90% of the product obtained is the compound of formula 1.

The process of this invention is especially useful for purifying the compound of formula 2. Although compound 2 crystallizes, it does not crystallize as readily as compound 1. Because of this, it is advantageous to crystallize hydrochoride salt 1, separate it from the impurities, and then prepare the free base 2 from the separated salt.

Methods of separating the crystalline salt, such as by filtration, are known in the art. Methods of preparing free base 2 from the crystalline salt 1 are also well known. Compound 2 can be prepared by treating compound 1with base, but this procedure is slow because compound 2 is very insoluble. A preferred method of preparing compound 2, therefore, comprises adding crystalline salt 1 which has been separated but not dried to an aqueous bicarbonate solution, maintaining the pH between about 6 and about 7, filtering to separate impurities, and precipitating compound 2 by careful addition of hydrochloric acid, preferably 4 N hydrochloric acid.

The following examples further illustrate the invention herein described.

EXAMPLE 1

Crystallization of the Hydrochloride Salt

Compound 2 (10 g) was dissolved with warming in formamide (25–30 ml). To this solution water (50 ml) was added. The resulting solution was acidified by the addition of 12 N HCl until the solution had a pH of about 1.5–2.0. This solution was cooled in a refrigerator for several hours until crystallization appeared complete. The crystals which formed were separated by filtration, washed with acetone, and air-dried to give the crystalline hydrochloride salt of formula 1 (80% yield).

EXAMPLE 2

On a larger scale the procedure described in Example 1 was repeated, using 1 kg of compound 2 and obtaining 810 g of crystalline hydrochloride salt 1. A portion of this lot was recrystallized using the same procedure to give highly purified crystalline hydrochloride 1. This material had a purity of 99.3%, after correcting for 11.1% water content.

EXAMPLE 3

Alternate Crystallization of the Hydrochloride Salt

Compound 2 (25 g, 0.0628 m) was added to ethanol (100 g) at about 35° C., stirring under nitrogen. Concentrated HCl (1.2 equivalents, 6.29 ml, special grade 1.18 g/ml) was added. The resulting suspension became a thick solution when warmed to 40° C., and crystallization began to occur. The mixture was stirred slowly for 3 hours at room temperature to permit complete crystallization. The crystals which formed were separated by filtration, washed with acetone, and air-dried for 2 hours at 45° C. to give 22.48 g of the crystalline hydrochloride of formula 1 (82.4% yield).

The above procedure, carried out on a larger scale, gave the crystalline hydrochloride 1 in 91.7% yield. UV: A 450=0.165 (5% solution in methanol); $E_1\,{}_{cm}^{1\%}$ =341; 10.06% water (Karl Fisher).

I claim:

1. The process for purifying the compound of formula 2:

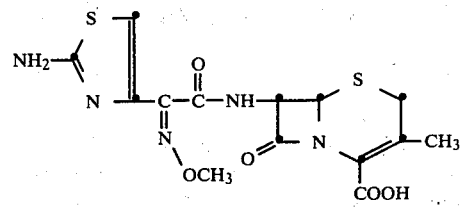

wherein the oxime is in the syn configuration which comprises preparing the crystalline hydrochloride salt of the formula 2 compound by (a) adding this compound to a solvent selected from water or a polar organic solvent to form a solution or slurry; (b) adding hydrochloric acid to give a solution which has a pH of between about 1.5 and 3.5; (c) maintaining the solution until crystallization occurs; (d) separating the crystalline salt; (e) dissolving the crystalline salt in an aqueous bicarbonate solution with the pH maintained between about 6 and about 7; (f) filtering the solution to separate solid impurities; and (g) adding hydrochloric acid to the filtered solution until free base of formula 2 precipitates.

2. The process of claim 1 wherein the solvent in step (a) is formamide.

3. The process of claim 1 wherein the solvent in step (a) is ethanol.

4. The process of claim 3 wherein the temperature of step (a) is between about 30° to about 45° C., the amount of hydrochloric acid in step (b) is from about 1 to about 2 equivalents, and the solution in step (c) is stirred at a temperature of between about 30° to about 45° C. until the compound is in solution and then is cooled to room temperature or below until crystallization occurs.

* * * * *